United States Patent
Xie (10) Patent No.: US 7,122,214 B2
(45) Date of Patent: Oct. 17, 2006

(54) DRYNARIA EXTRACTIONS FOR TREATING OSTEOPOROSIS AND THEIR EXTRACTION PROCESS

(75) Inventor: Yanming Xie, Beijing (CN)

(73) Assignees: Qihuang Pharmaceutical Technology and Investment Co., Ltd., Beijing (CN); Xiyuan Hospital Affiliated to China Academy of TCM., Beijing (CN)

( * ) Notice: Subject to any disclaimer, the term of this patent is extended or adjusted under 35 U.S.C. 154(b) by 0 days.

(21) Appl. No.: 10/451,966

(22) PCT Filed: Dec. 29, 2000

(86) PCT No.: PCT/CN00/00739

§ 371 (c)(1),
(2), (4) Date: Aug. 27, 2003

(87) PCT Pub. No.: WO02/053164

PCT Pub. Date: Jul. 11, 2002

(65) Prior Publication Data

US 2004/0048811 A1    Mar. 11, 2004

(51) Int. Cl.
*A61K 36/00*    (2006.01)

(52) U.S. Cl. ...................................... 424/773; 424/725
(58) Field of Classification Search ................. 424/773
See application file for complete search history.

(56) References Cited

FOREIGN PATENT DOCUMENTS

| CN | 1075598 | 6/1993 |
|---|---|---|
| CN | 1116938 | 2/1996 |

OTHER PUBLICATIONS

Effects of Gushikangfuwan on osteoporosis induced by retinoic acid in rats, (Chinese pharmacological Journal), Wang Shuling etc. 1999,34(2), p. 138-141.
Study of the fatsoluble ingredients in drynzaria, (Chinese Traditonal Mediciane Journal), Liu Zhenli etc. 1999,24(4), p. 222-223.

Primary Examiner—Susan D. Coe
(74) Attorney, Agent, or Firm—Ladas & Parry LLP (57) ABSTRACT

*Rhizoma Drynariae* extract (RDE) is used as therapeutical agent or in the preparation for Osteoporosis, which is characterized in containing over 30 percent of total flavonoids. Furthermore naringin contained in flavonoids is more than 30 percent and less than 100 percent. The RDE is applied for the therapy of osteoporosis or used for producing drugs treating osteoporosis. And methods of extracting the same are also related.

21 Claims, 6 Drawing Sheets

DRYNARIA EXTRACTIONS FOR TREATING OSTEOPOROSIS AND THEIR EXTRACTION PROCESS

FIELD OF THE INVENTION

The present invention relates to *Rhizoma Drynariae* Extract (RDE), more specifically to a RDE for the treatment of osteoporosis, and the preparation process of such and the use thereof in the treatment of osteoporosis. The present invention is also related to the method of treating osteoporosis with the extract.

BACKGROUND OF THE INVENTION

*Rhizoma Drynariae* is the rhizome of *Drynaria fortunei* (Kunze) J. Sm or *D. baronii* (Chist) Diels, which is used for the treatment of bone fracture for a long time (*Zhong Yao Da Ci Dian* (*Lexicon of Traditional Chinese Medicine*), 1658–1660, Shanghai People's Press, ShangHai, 1979). Ma Ke-Chang et al., studied the influence of *Rhizoma Drynariae* on rat Osteoporosis model, the results showed that *Rhizoma Drynariae* extract partically restrains the glucocorticoid-induced bone loss (Ma Ke-Chang et al., *Zhong Yi Zheng Gu* (*Bone Setting*) 1992, 4, 3), but the active component therein is unknown. Additionally, Zhou Tong-Shui et al. reported that the effective component of *Rhizoma Drynariae* for treating bone injury is naringin and analogues thereof (Zhou Tong-Shui, et. al., *Zhong Cao Yao* (*Chinese Herbal Medicine*) 1994, 25, 249). And they also performed assaying in crude plant of *Rhizoma Drynariae* (Zhou Tong-shui et al., *Zhong Guo Yao Ke Da Xue Xue Bao* (*Journal of China Pharmaceutical University*), 1996, 27, (9), 540), but they didn't show the relationship between the above-mentioned active components and the effect to Osteoporosis thereof.

Wu Ying-Pi et al. disclosed a method of extracting naringin from *Citrus grandis* Osbeck var. *tomentosa* Hort, aiming to obtain the single component of naringin (Wu Ying-Pi et al., *Zhong Cao Yao*, 1988, 19, 452) only. Therefore, it is unknown whether or not such method can be fitted for other medicinal materials.

SUMMARY OF THE INVENTION

The object of the present invention is to provide *Rhizoma Drynariae* extract (herein after also referred as RDE), which is available for the treatment of Osteoporosis.

The other object is to provide a composition comprising RDE and the use of which for the treatment of osteoporosis.

Another object is to provide a process of preparation of RDE.

One further object of the present invention is to provide a composition comprising naringin for the treatment of osteoporosis, and the treatment method of osteoporosis with the composition.

The technical embodiments of the present invention are as following:

1. An extract from *Rhizoma Drynariae*, wherein the content of total flavonoids, based on the weight of the extract, is 30% or more, and the content of naringin thereof, based on the weight of total flavonoids, is 30% or more, and less than 100 percent.

2. The extract according to 1, wherein the content of total flavonoids is 50% or more.

3. The extract according to 2, wherein the content of naringin is 90% or less.

4. A pharmaceutical composition comprises the extract of 1.

5. The composition according to 4, which is used for the treatment of osteoporosis.

6. Use of the extract according to 1 in the preparation of medicaments for the treatment of osteoporosis.

7. Use of the extract according to 1 for the treatment of osteoporosis.

8. A preparation process of the extract according to 1, comprising:
   1) extracting *Rhizoma Drynariae* with water, alcohol or a mixture thereof;
   2) adsorbing of the extractant with resin; and
   3) elution of the resin which has absorbed the extractant with water, alcohol or a mixture thereof.

9. The preparation process according to 8, wherein the extraction is conducted with water.

10. The preparation process according to 8, wherein the extraction is conducted with alcohol/water mixture.

11. The preparation process according to 8 or 10, wherein the content of alcohol in the alcohol/water mixture is 40–90% (w/w).

12. The preparation process according to 8, 10 or 11, wherein the alcohol is selected from methanol and ethanol.

13. The preparation process according to 12, wherein the alcohol is ethanol.

14. The preparation process according to 13, wherein the resin is macropore adsorption resin.

15. The preparation process according to 8 or 14, wherein said resin is washed by water after adsorption of the extractant, before the elution with alcohol or alcohol/water mixture.

16. The preparation process according to 15, wherein the extraction is conducted with alcohol/water mixture.

17. The preparation process according to 15 or 16, wherein the content of alcohol in the alcohol/water mixture is 40–90% (w/w).

18. The preparation process according to 15, 16 or 17, wherein the alcohol is selected from methanol and ethanol.

19. The preparation process according to 18, wherein the alcohol is ethanol.

DETAILED DESCRIPTION OF THE INVENTION

In the following descriptions of the present invention, percentage represents weight percentage, unless specifically identified.

In the present invention, *Rhizoma Drynariae* may be the rhizome or the whole plant of the plants from the genus *Drynaria* (Bory) J. Sm, *Polypodiaceae* S. F. Gary, such as *Drynaria fortunei* (Kunze) J. Sm, *D. baronii* (Chist) Diels,

*D. sinica* Diels, and *D. delavayi* Chirst, et al., or *Davallia mariesii* Moore ex Bak from the genus *Davallia* Sm, and the like. In the present invention, plants used as *Rhizoma Drynariae* may be from one single species or a mixture of multiple species as described above, and is not limited.

The inventors have conducted an intensive investigation and found that particular extract from *Rhizoma Drynariae* or the single compound naringin have the activity of improving osteoporosis. Among the extract possessing activity against osteoporosis, the content of total flavonoids is always more than 30%, and content of naringin in the flavonoids is more than 30%. The compound naringin per se also has the activity of improving osteoporosis, whereas the efficiency thereof is lower than the active extracts described above.

In the present invention, the total flavonoids contained in RDE should be 30% (wt %) or more, preferably 40% or more, more preferably 45% or more, and most preferably 50% or more. Though there is no particular upper limit for the content of total flavonoids, which can be ranged from 30% to 100% in the extract, however, while considering the balance of the choice of process and cost, as long as content of total flavonoids is 50% or more, the object of this present invention can be well achieved. If the content is upper than 90%, it does not only cost more, but extra procedure is also needed. Therefore the most preferable total flavonoids content ranged from 50% to 90%.

According to the present method, the RDE of present invention also comprises polyphenol compounds. Although there is no evidence for polyphenol compounds against osteoporosis, but the extract of present invention may preferrably contain polyphenols, for polyphenols have the activity of anti-oxidization, therefore the polyphenol compounds may be helpful for the present extract in the use of preperation of pharmaceuticals. The content of polyphenols may vary depending on different processes, but the contents are normally ranging from 10% to 50%.

In the present invention, naringin's content should be 30% or more, preferably 40% or more, and more preferably 50% or more, with respect to total flavonoids, but naringin shouldn't be the only flavonoid of total flavonoids, preferably no more than 90%, and more preferably no more than 80%.

We have extracted the flavonoids containing extract of *Rhizoma Drynariae* (as defined above). The results of experiments and clinical trials have shown that the *Rhizoma Drynariae* extract produced by the process of present invention has reliable effects on osteoporosis.

Although it is not proved by any known theories, but it is reasonable that the activity of anti-osteoporosis of the present extract is not only rooted in naringin, but also some other components which may have the synergic effects with naringin. Under the limitations of present invention, such components co-present with naringin and show the activity of anti-osteoporosis.

The producing process of *Rhizoma Drynariae* extract is discussed herein after.

A typical producing process may comprise the following steps: [Crude drug pulverizing]→water/alcohol decoction→resin adsorption→(water washing)→alcohol/water elution—post procession Among the process, means to pulverize *Rhizoma Drynariae* are common processes to those skilled in the art and are not limited. If the granularity of powder is too coarse, the active components will not be sufficiently extracted; if the granularity is too fine, the separation of extracted solution after decoction may be difficult. Such can be readily determined by the experience of those skilled in the art, and will not be limited.

In order to extract effective component, soaking extraction by water and/or alcohol may also be adopted. However, since the effective component may not be lixiviated completely, heat extraction is preferred, the heating temperature may range from room temperature to the boiling point of extracting solvent.

The temperature in heat extraction is preferably conducted at the boiling point of extracting solvent (reflux).

In case when the crude drug is extracted with water along, the extraction is conducted under 100° C. for 0.5–3 hrs and repeated for 2–4 times, while the volume of water is 5–20 folds by weight of crude drug each time. In case when extraction is conducted with alcohol or alcohol aqueous solution under reflux temperature, the crude drug is extracted for 0.5–3hrs and repeated for 2–4 times, while the volume of solvent is 5–20 folds by weight of crude drug each time. The alcohol may be methanol or ethanol, and ethanol is preferred from the viewpoint of safety. When adopted, the concentration of ethanol is preferably in the range of 20–90%. And all the data mentioned above are for reference only. It can be modified based on the experience of person of the art, and it should be understood that such changes are not beyond the scope of the present invention.

If desired, the extractant obtained may firstly be filtrated, then adsorbed by resin, which may be macropore adsorption resin, such as $D_{101}$ resin (manufactured by Nankai University Resin Factory, Tianjin), AB-8 resin (manufactured by Tianjin Bone-gel Factory), WLD resin (manufactured by the Chinese Traditional Medicine Institute of Sichuan Province) and CAD-40 resin (manufactured by Huabei Pharmaceuticals), etc. The method of this present invention is not limited by the model of resins. The detailed description of resin adsorption is described in CN1072089A, and referred herein with the present invention and incorporated as a part of it.

According to the research of the present inventors, WLD resin has the highest adsorption capability among the resins mentioned above, and is much easier to be eluted. So use of WLD resin as adsorbent is preferred. The ratio of the amount of resin to crude drug may range from 0.5–2:1 (w/w), preferably 0.5–1.5:1, most preferably about 1:1, which can be well determined by those of the art. If the ratio is less than 0.5:1, it is likely to adsorb incompletely. If it is more than 1.5:1, the adsorbed flavonoid may not increase much more, and may cause economical disadvantages.

While employing adsorption resin, according to the common knowledge well known by those of the art, the resin should be pretreated via known methods before using, for example the resin might be pretreated as following:

packing the resin in a column, rinsing the column with ethanol-conc. HCl (1:1) until the effluent fluid is clear upon dilution with a equivolume of water, then flushing the column with hot water (about 80° C.) tenfolds volume of the resin column, after that, rinsing the column with 2% sodium hydroxide -equivolume of the resin column, and finally rinsing with water until the effluent fluid become neutral.

The resin is then reverse-rinsed with water to loose, and then upload the solution to be eluted.

During absorption, the flow-rate should be controlled to ensure complete adsorption. Generally, at the time of industrial manufaction, while a column (φ 360 mm) packed with 100 kg of resin is employed, the adsorption may be ensured to be complete if the flow-rate be adjusted to 10–20 $L \cdot min^{-1}$.

In such case, if the flow-rate is more than 20 L·min$^{-1}$, it is hard to adsorb completely, the yield may be lowered; if it is less than 10 L·min$^{-1}$, it is disadvantageous for increasing the productivity.

After adsorption, the resin may be eluted by alcohol such as ethanol or methanol, ethanol is preferred from the viewpoint of healthy. When using ethanol, the concentration of which is preferably 50–95%, and the most preferred is 70% (may±about 5%) in consideration of the reutilization of ethanol.

While eluting, the ratio of the amount of alcohol to crude drug may range from 2 to 10. If the ratio is less than 2, the elution is incomplete, if it is more than 10, the eluted components will not increase further and is economically disadvantageous. In view of manufacturing, 2–5 folds is preferred.

After elution, the eluent is collected and concentrated after removing of ethanol for reutilize. Finally, brown or umber powder is obtained via spray-drying, lyophilizing or normal drying and pulverizing. The powder can be refined or directly filled into the proper preparations, such as capsules, pills, tablets, granules, solutions or injections.

Relative density of the residue is adjusted to 1.10–1.18 before spray-drying, and is adjusted to 1.3–1.4 before vacuum drying. After drying, the product may be pulverized to fine powder to facilitate the further processes. Spray-drying and vacuum drying are ordinary techniques of drying and is not limited.

The *Rhizoma Drynariae* extract of present invention as described above may be prepared into any pharmaceutical preparations suitable for clinical uses, such as capsules, pills, tablets, granules, solutions or injections upon ordinary preparation procedures. The dosage of each type of preparation may vary depending on the composition of formulation, status of the patient and clinical conditions. General, in case when the content of total flavonoids in RDE is 50%, the oral administration dosage may be 0.1–5.0 g/day in 1–4 portions per patient.

The *Rhizoma Drynariae* extract of present invention has outstanding activity of improving osteoporosis. The following Examples are provided to illustrate the invention and do not limit it in any way.

EXAMPLES

The flavonoids in the RDE is qualitative characterized by potassium borohydride (KBH$_4$) color-reaction. And the elution termination is determined by thin layer chromatography (TLC). And ultraviolet (UV) spectrometry is applied to quantitative analysis of total flavonoids. High-performance liquid chromatography (HPLC) is applied to quantitatively analyze naringin.

Potassium borohydride color reaction: KBH$_4$ (about 5 mg) is added into a test tube containing about 5 ml of sample solution and shaken up, into which several drops of hydrochloric acid is added, the appeared cherry red or fuchsia shows the existence of dihydroflavonone (sensitivity 55 μg/ml). Otherwise it is negative if it doesn't appear cherry red or fuchsia.

TLC: Naringin standard in methanol to the concentration of 0.5 mg/ml is used as control solution. Based on the TLC method in accordance with *Pharmacopoeia Sinica* (1995) *appendix VI B*, each of 4 μl of control and test solutions are applied to one silica gel-G plate, after that eluted with the upper layer of the mixture of benzene-ethyl acetate-formic acid-water (1:12:2.5:3). After elution, the plate is taken out and aired, sprayed by aluminum chloride (AlCl$_3$) solution and finally determined under UV light at 365 nm. The test sample shows a fluorescence blot same color as that of the control in the corresponding site of the plate.

UV Spectrometry Quantitative Analysis of Total Flavonoids:

This analysis is based on the UV spectrophotometric method in *Pharmacopoeia Sinica* (1995) *appendix VA*.

Preparation of control solution: 10 mg of Hesperidin standard, which is desiccated under 105° C. to constant weight, is precisely weighed and dissolved in methanol (100 ml) in a volumetric flask (100 ml). (Final concentration: 0.1 mg/ml)

Standard curve: Standard solutions of 0.50 ml, 1.00 ml, 2.00 ml, 4.00 ml, and 5.00 ml are precisely pipetted and diluted with methanol to 25 ml of volume respectively. Methanol is used as the blank control. UV detection is performed in accordance with *appendix VA*), and absorbency is determined at 284±1 nm. The calibration curve is plotted with the X-axis of concentration and the Y-axis of absorbency.

Sample solution preparation: testing sample (0.25 g), which is precisely weighed, is dissolved in methanol (50 ml) in conical flask, ultrasonic extracted for 30 minutes, and transferred to a volumetric flask (100 ml) after cooling. And the conical flask is washed with methanol the rinsing liquid is also transferred into the volumetric flask. And the solution is diluted by methanol to 100 ml, and then filtrated. The subsequent filtrate is collected, and a precise volume 1 ml of the filtrate is applied to a chromatograph column (packed with 0.5 g of polyamide as solid phase, which has passed 60 mesh of shieve). Then the column is eluted by methanol with a flow rate of about 0.4 ml/min. About 25 ml of eluent is collected and diluted by methanol to a volume of 100 ml.

Measurement: According to the UV spectrophotometric method in *Pharmacopoeia Sinica* (1995) *appendix VA*, the absorbency of the sample solution is detected, and then the total flavonoids concentration is read from the standard curve.

Instruments and reagents: ultraviolet spectrometry, model UV-260 (Shimazu Inc., Japan), hesperidin standard (from the *National Institute for the Control of Pharmaceutical and Biological Products*)

HPLC Determination of Naringin

The test is based on the HPLC method of *Pharmacopoeia Sinica* (1995) *appendix VI D*.

Chromatographic conditions: C-18-alkylsilane-bonded-silica-gel is used as solid phase, a mixture of methanol-(36% acetic acid)-water (35:4:65) is used as mobile phase, detecting wavelength at 283 nm. Number of theoretical plates is calculated from the peak of naringin, and should be no less than 3000.

Preparation of control solution: Naringin standard, which is desiccated under 105° C. to constant weight, is precisely weighed and dissolved in methanol and diluted with methanol to the final concentration 50 μg/ml.

Preparation of sample solution: the product (ca. 0.2 g) is precisely weighted and put into 150 mL conical flask, 60 mL of methanol is added therein. After 30 mins of ultrasonic extraction, the solution is taken out and cooled to room temperature. Afterwards the sample solution is transferred into a 100 mL volume volumetric bottle. The conical flask is washed with methanol and methanol is combined into the bottle. The obtained solution is diluted to 100 ml by methanol, shaked to uniform and filtrated. The subsequent filtrate is collected, 2 ml of the filtrate is precisely pipetted into a 25 ml volumic bottle and diluted with methanol to the volume to obtain the sample solution.

Measurement: Control solution (10 μl) and sample solution (10 μl) is respectively injected into the HPLC system for analysis.

Instruments and reagents: HPLC: LC-6A (Shimazu Inc., Japan); UV detector: SPD-6AV; data processor (C-R4A), sensibility of data recorder 0.16AUFS; Chromatograph Column: Shimpack $C_{18}$ column (CLC-ODS 150×6.0 mm i.d., 5 μm); Protecting Column: YMG $C_{18}$ column (10×4.6 mmi.d., 10 μm); Supercentrifuge: TGL-16G (Shanghai Medical Analytical Instruments Factory); Ultrasonic cleaner: SB 3200 (Shanghai Bi'nengxin Ultrasonic Company, Ltd)

Figure 1:
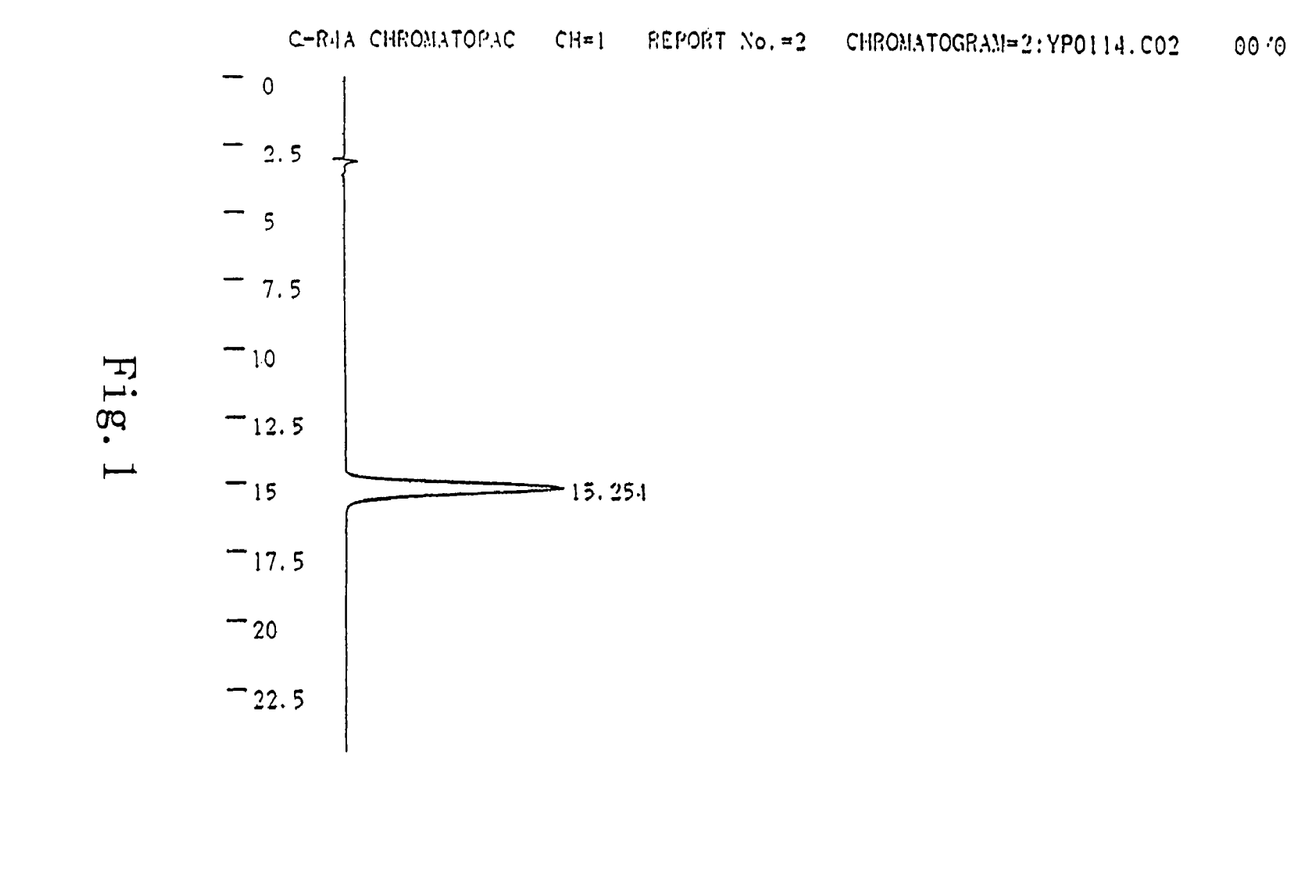
FIG. 1 shows HPLC chromatograph of standard naringin as control.

Standards of naringin are obtained from *National Institute for the Control of Pharmaceutical and Biological Products*. Under the above spectrum conditions, it is calculated that naringin contained in the present standards is more than 98% by normalized method (see FIG. 1). Under the present experimental conditions, the peak of naringin is appeared at the retention time of about 15.26 min.

All the reagents and solvents used in the examples are analytically pure grade. Water is double-distilled.

Example 1

100 grams of *Rhizoma Drynariae* was pulverized and decocted in 1500 ml of water for 1 hour, the extract liquid was removed and additional 1000 ml of water was added and detocted again. The two detection liquids were combined and filtrated. The filtrate was applied to a pretreated column (φ 30 mm) packed with 120 g of WLD resin at a flow rate of 4 ml/min, and the terminated point of effluent collection was determined by $KBH_4$ color reaction, that is, the sudden appearance of dihydroflavonone showed the saturation of adsorption in the effluent-resin. After adsorption, the column was washed with 500 ml of water and washing liquid was not-recycled. Elution was conducted with 400 ml of 70% ethanol. The starting and end point of elution was determined by $KBH_4$ color test, eluent was collected and ethanol was recycled. Residual was evaporated on a water bath to give thick paste, which was then dried in vacuo to afford 1.88 g of extract. Thus obtained RDE had a total flavonoids content of 55.08% detected by UV spectrometry, and a naringin content of 36.6% (i.e. 66.4% of the total flavonoids) determined by HPLC.

Figure 2:
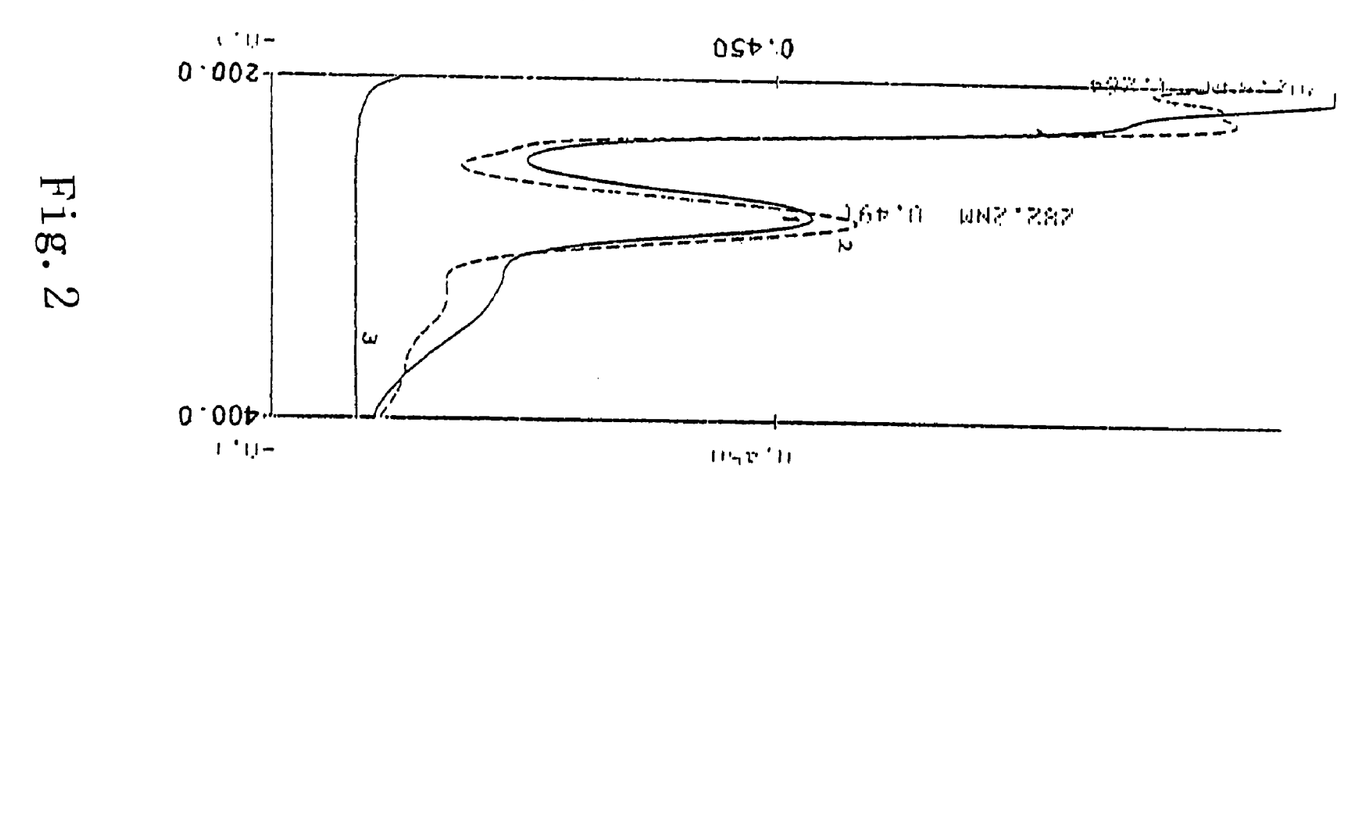
FIG. 2 shows the UV spectrographs of standard naringin, the solution of the extract of Example 1 and blank solution.

FIG. 2 shows the UV spectrum of the solutions of RDE, naringin, and blank control (X-axis: wave length; Y-axis: absorbency; 1: naringin standard; 2: present extract; 3: blank). From the UV spectrum, great differentiation can be observed between RDE and naringin. RDE has an absorption peak at around 200 nm, whereas naringin has only a shoulder peak at that wavelength. And there is also difference in the maximum absorption wavelength.

Figure 3:
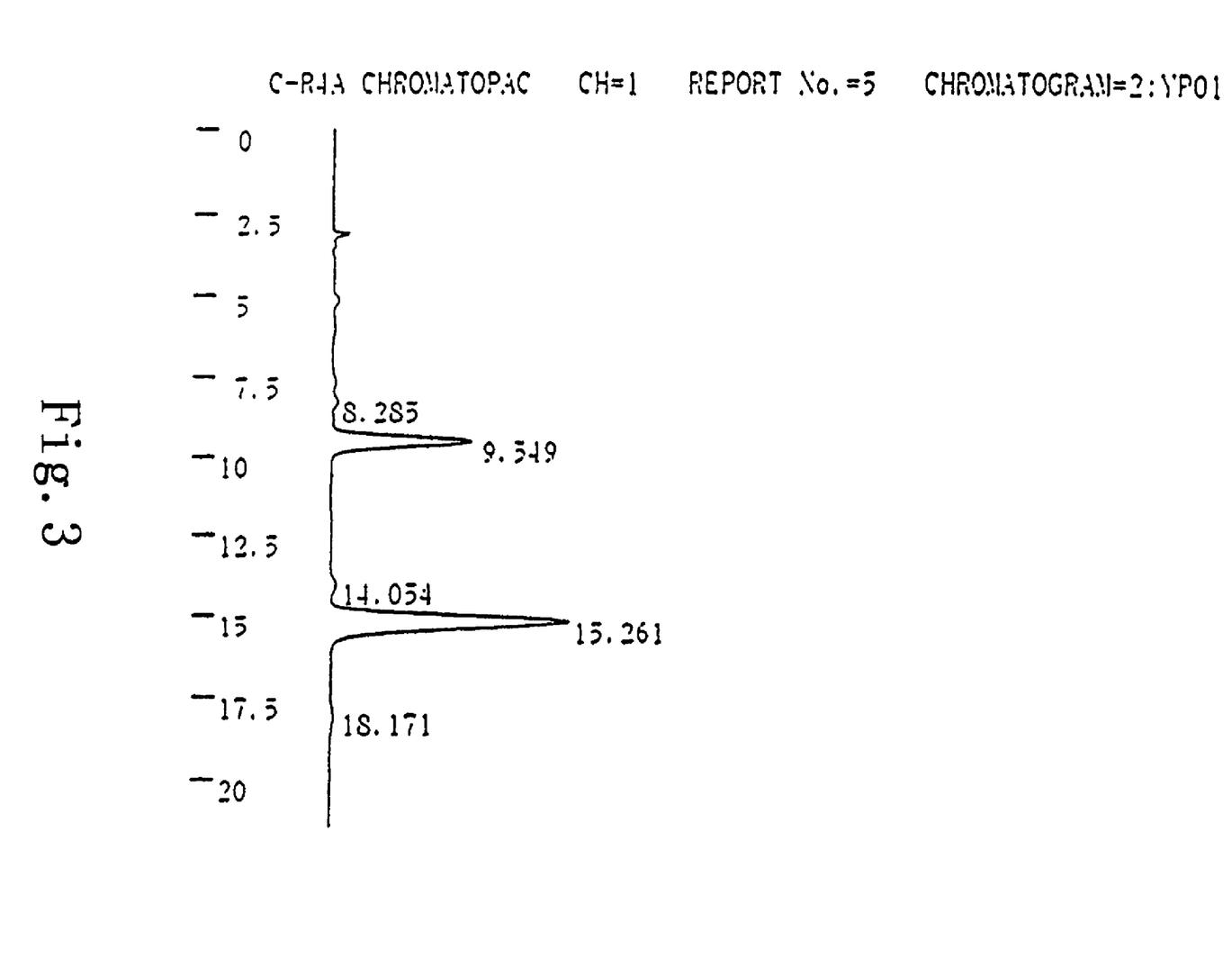
FIG. 3 shows HPLC chromatograph of the extract of Example 1.

The high-performance liquid chromatogram of the extract is shown in FIG. 3, in which there is at least one another unknown compound co-existing in the extract. (X-axis: Retention time; Y-axis: Integral intensity).

Example 2

In the same manner as that of Example 1 except that 70% of ethanol was used for reflux and elution solvent. A 1.69 g of extract was obtained, in which the total flavonoids content was 53.12%, and naringin is 32.5% determined by HPLC (61.2% of the total flavonoids).

Figure 4:
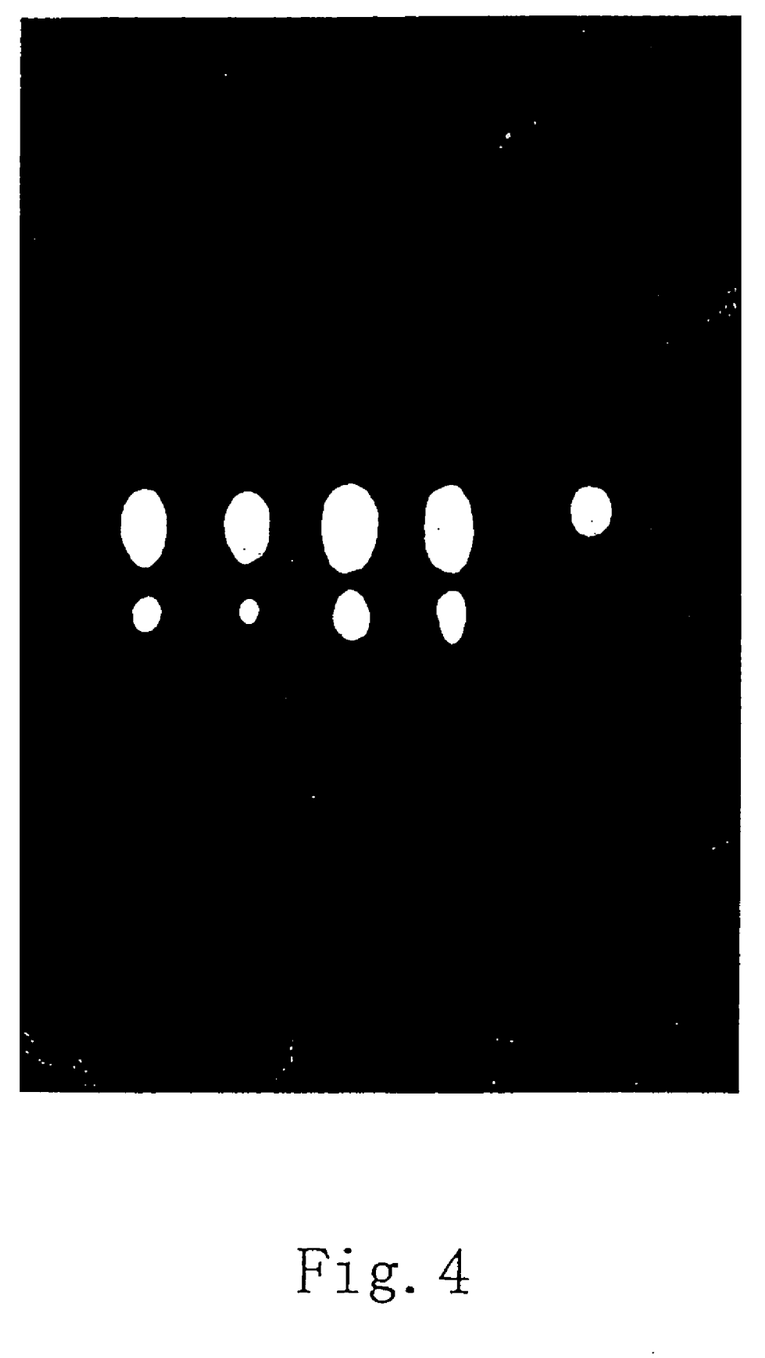
FIG. 4 shows the comparison of TLC chromatographs of the solutions of the extracts from different processes.

The comparison of TLC for several extracting solutions extracted by different processes are shown in FIG. 4, in which from left to right are chromatograms of extractant and extract of example 1, extractant and extract of present example, and naringin. From the results can we see that the extracts are substantially same no wonder extracted by water or alcohol.

Example 3

Figure 5:
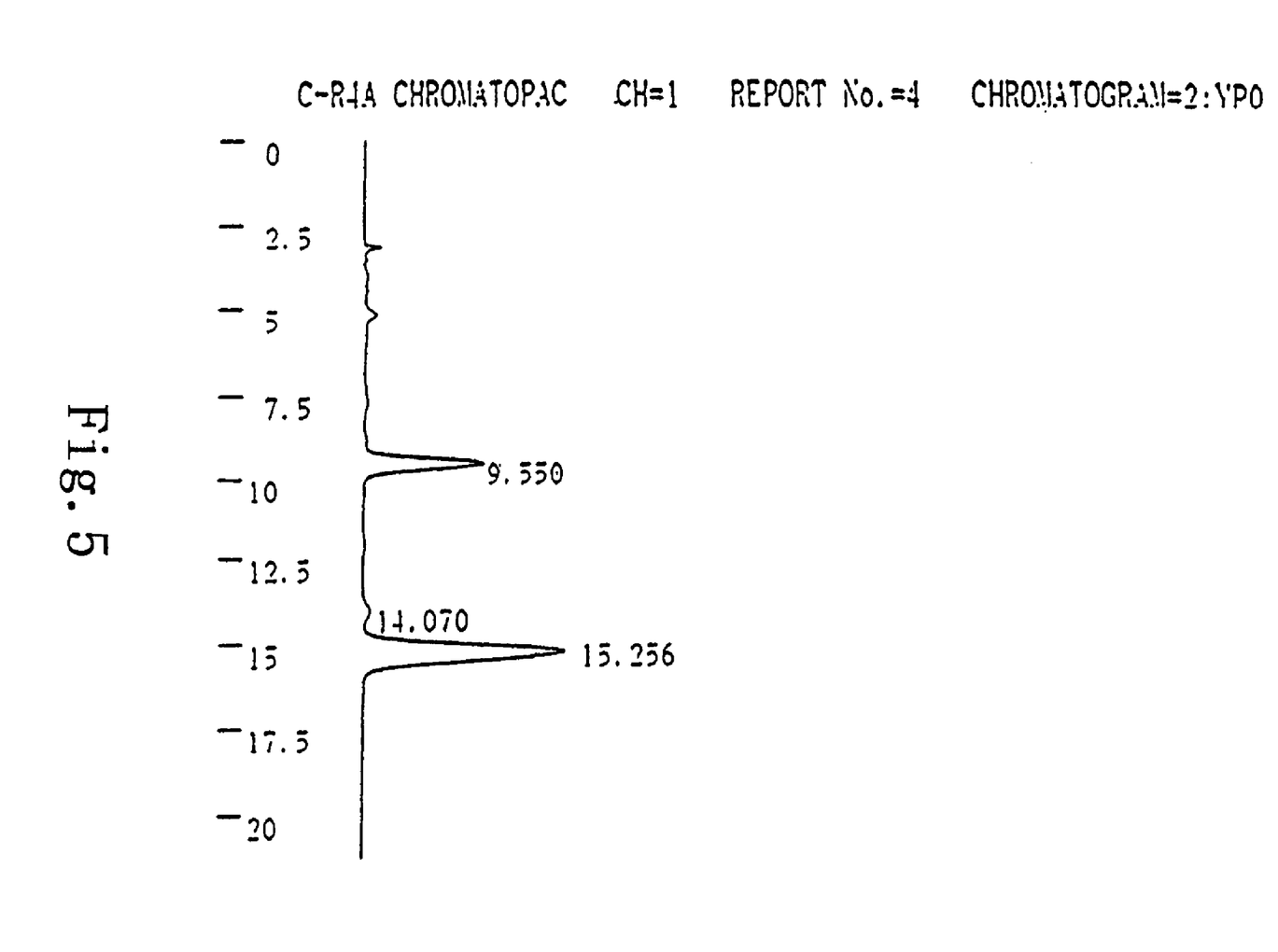
FIG. 5 shows HPLC chromatograph of the extract of Example 3.

In the same manner as that of Example 1 except that AB-8 resin was used instead of WLD resin. A 0.95 g of extract was obtained, with the total flavonoids content of 61.80%. FIG. 5 shows the HPLC of the extract of Example 3.

Example 4

Figure 6:
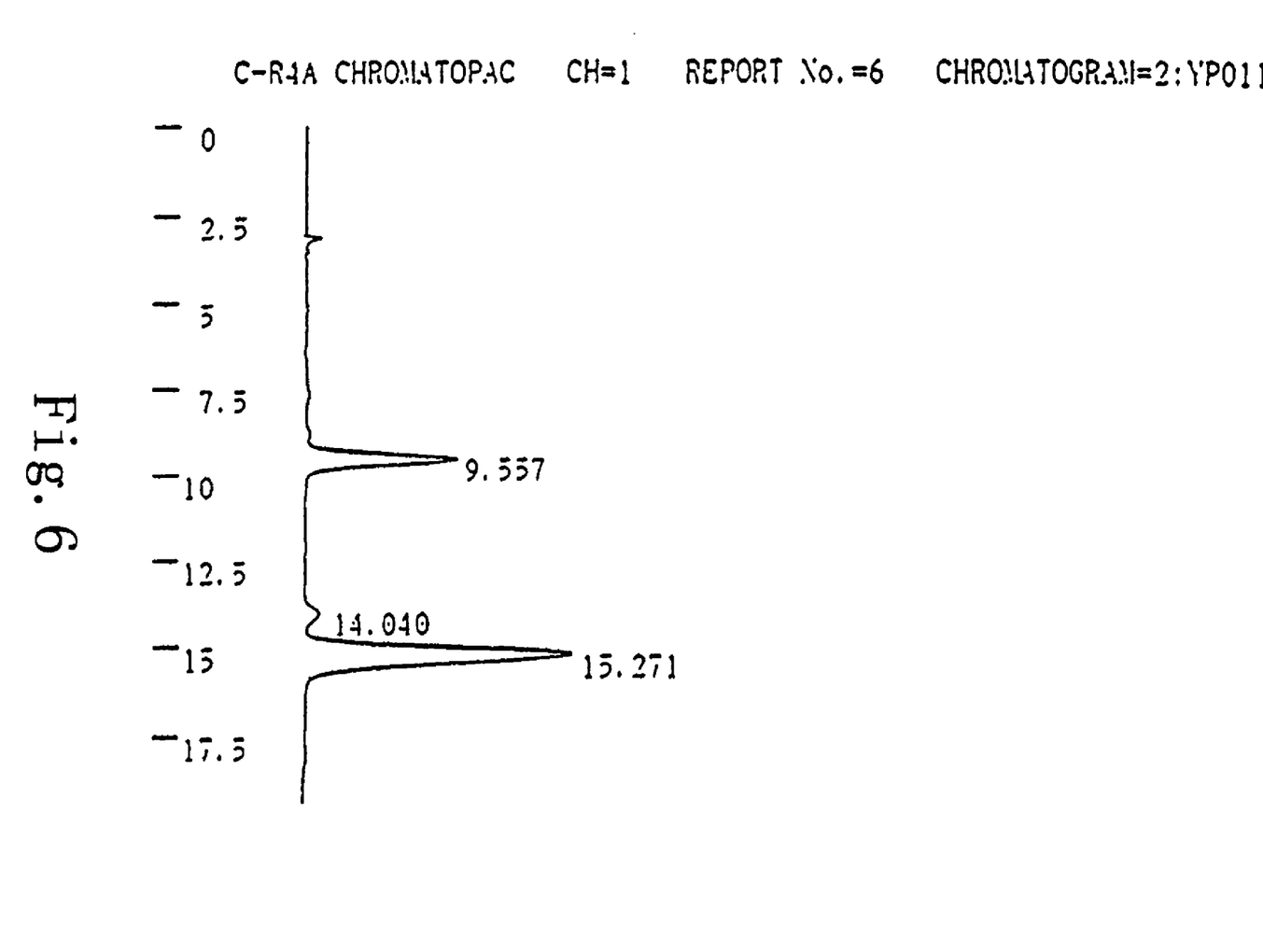
FIG. 6 shows HPLC chromatograph of the extract of Example 4.

In the same manner as that of Example 1 except that $D_{101}$ resin was used instead of WLD resin. A 1.07 g of extract was obtained, with the total flavonoids content of 57.35%. FIG. 6 shows the HPLC of the extract of in Example 4.

From FIGS. 3, 4 and 5 can we see that although different types of resin was used as the adsorbent, the composition and content ratio of flavonoids in the extracts are generally the same.

Example 5

In the same manner as that of Example 1 except that 10 g of *Rhizoma Drynariae* power was used each time, and 5 g, 10 g, 20 g and 25 g of resins were used respectively. 0.16 g, 0.20 g, 0.27 g and 0.27 g of the extract were obtained accordingly, wherein the total flavonoids contents are 53.88%, 52.29%, 42.65% and 41.88%, respectively. The yield of total flavonoids were 86.2 mg, 104.6 mg, 115.2 mg and 113.1 mg, respectively, and the total flavonoid ratio are 0.86%, 1.05%, 1.15% and 1.13%, respectively. The above data shows that the total flavonoids extracted from the same amount of crude drug is almost not increasing when the weight ratio of crude drug to resin is more than 1:2, which means that the adsorption is complete when the resin is 2× the amount of the crude drug. When weight ratio of crude drug to resin is 1:1, the total flavonoids in adsorbate is relatively higher: the extract has an is amount of 90.8% of the full adsorption, with the total flavonoids content of 52.29%. Therefore, a ratio at about 1:1 of crude drug: resin is preferred.

Example 6

A 40 g of pulverized *Rhizoma Drynariae* was decocted with 1000 ml of water for 1 hour (slow fire), and the decoctate was filtrated and divided into four portions averagely. Four glass columns (φ 20 mm) were packed with pretreated WLD macropore adsorption resin (10 g). Every portion of decoctates was applied to one column respectively at different flow rates of 2 ml/min, 4 ml/min, 8 ml/min and 16 ml/min, and $KBH_4$ color reaction was applied to test whether there was flavonoid glycoside in the effluent. Results are shown in table 1.

TABLE 1

| Flow rate (ml/min) | Effects | Flavonoid in effluent |
| --- | --- | --- |
| 2 | Completely adsorbed | − |
| 4 | Completely adsorbed | − |
| 8 | Incompletely adsorbed | + |
| 16 | Incompletely adsorbed | + |

It can be concluded that the control of flow rate ensures complete adsorption.

Example 7

A 300 g of raw pulverized *Rhizoma Drynariae* was treated in the same manera as Example 1 to obtain the filtrate. And the filtrate was divided to three portions averagely, each was applied to the column (φ 40 mm, packed with 100 g of WLD resin), then eluted with ethanol of different concentrations. The eluent was concentrated and dried, the total flavonoids contents were measured via UV spectrometry. The results are shown in table 2.

TABLE 2

| Ethanol concentration (%) (Group) | 0% | 50% (1) | 70% (2) | 95% (3) |
| --- | --- | --- | --- | --- |
| Total flavonoids (g) | 0 | 1.668 | 1.888 | 1.587 |
| | 0 | 1.672 | 1.843 | 1.531 |
| | 0 | 1.679 | 1.871 | 1.574 |
| $\bar{x} \pm SD$ | 0 | 1.673 ± 0.006 | 1.876 ± 0.023 | 1.564 ± 0.024 |

It can be concluded that the concentration of ethanol affects the effect of elution, in which the concentration of about 70% is preferred.

Example 8

Raw powder of *Rhizoma Drynariae* (500 g) was treated as the same manner that of Example 1 to obtain the filtrate, which then is applied to a column (weight ratio of crude drug to resin is 1:1). After adsorption, the resin was eluted with 70% ethanol in the volume of 1×, 2×, 3×, 5×, 7× and 10× amount of crude drug (v/w), the eluents were collected separately, from which the ethanol was recycled. Then the total flavonoids was measured separately. The results show that the elution is complete when elution by 10 folds of ethanol, which is shown in table 3.

TABLE 3

| | 70% ethanol | | | | | |
| --- | --- | --- | --- | --- | --- | --- |
| | 1× | 2× | 3× | 5× | 7× | 10× |
| Sorbent (%) | 0.47 | 8.76 | 1.99 | 0.47 | 0.44 | 0.22 |
| Flavonoids (%) | 0.21 | 53.11 | 64.26 | 51.42 | 24.87 | 6.72 |
| Flavonoids (mg) | 0.987 | 4652.436 | 1278.774 | 241.674 | 109.428 | 14.784 |
| % of total flavonoids | 0.016 | 73.871 | 20.304 | 3.837 | 1.737 | 0.235 |

Results in table 3 show that the total flavonoids can be eluted completely, when eluted by enough quantity of ethanol (10 folds). When the quantity of ethanol is 5 folds of RD, from which the total flavonoids is amounted to 98% of the total flavonoids.

Preparation Example 1

Capsule

To 180 g powder of RDE obtained in the same manner that of Example 1, 70 g of starch was added. The two components were mixed well and then filled into 1000 capsules. Each capsule contains 180 mg of effective component.

Preparation Example 2

Tablet

To 180 g powder of RDE obtained in the same manner that of Example, 70 g of starch was added. Then the mixture was kneaded with a small amount of aqueous CMC-Na and then pelletized, dried according to the ordinary methods, into which a small amount of magnesium stearate was added and mixed well to produce 1000 tablets. Each tablet contains 180 mg of effective component.

Preparation Example 3

Injectable Formulation

To 180 g powder of RDE obtained in the same manner that of Example, 800 ml of injectable distilled water was added. The resultant mixture was heated to solve, then filtrated by microporous filter membranes, stored for 24 hours at 4° C.–8° C., then filtrated again, adjusted pH to 6.5 and isotonic with medicinal grade aqueous HCl (12N) and NaOH (12N), finally injectable distilled water was added upto 1000 ml, sterilized by heating, and filtrated, then divide into ampoules (5 ml per ampoule). Each ampoule contains 180 mg of effective component.

Test Example 1

The Clinical Test of RDE of Present Invention on Primary Osteoporosis.

The drugs with the following dosages and contents are used unless additional explanations.

Extracts in this present invention: capsules of preparation example 1, each capsule contains 0.18 g of effective component. Positive control medicine: α-$D_3$, (synthesized by TEVA PHARMACEUTICALS, Israel, prepared by Sino-US Kunming BARKER NORTON PHARMACEUTICAL CO., LTD), each capsule contains 0.5 μg of effective component)

Diagnostic criteria: *Comprehensive Diagnostic Grades for Primary Osteoporosis*, according to the diagnostic criteria established by *Specialized Committee of Osteoporosis of Chinese Association of Geriatrics*. (cf. *Gu-zhi-shu-song-zheng* [M], p169–171, LIU Zhonghou eds. Chemical Industrial Press, Guangzhou, 1992)

According to the diagnostic criteria mentioned above, 70 cases of osteoporosis are randomly divided into treatment group with RDE and control group with α-$D_3$. RDE is administrated 180 mg, per os, tid, for 6 months-2 period of treatment. And α-$D_3$ is administrated 0.5 μg, per os, bid, for 6 months too.

Bone density of lumbar ($L_2$–$L_4$) and top-femur (collum femoris, trigonal area of femur, trochanteric of femur) is checked respectively by *Double-Energy X-ray Bone Density Meter* (LUNAR DPX-L DEXA bone densitometer,US). The unit is g/cm². And an *Ultrasonic Bone Densitometer* (model 2000-SYS-220, METRA Co., Israel) is employed to check the bone density of mid-portion of tibia.

The comparison of bone density pre- and after-treatment in two groups:

1. The results of bone density of lumber ($L_2$–$L_4$) pre- and after-treatment are shown in table 4:

TABLE 4

Bone density of lumber ($L_2$–$L_4$) before- and after- treatment in two groups ($\overline{X} \pm s$, g/cm$^2$)

| Group | Before-treatment | after- 3 months treatment | after- 6 months treatment |
|---|---|---|---|
| Treatment group (17) | 0.973 ± 0.124 | 1.038 ± 0.234 | 1.101 ± 0.303 |
| Control group (17) | 0.958 ± 0.180 | 0.954 ± 0.179 | 0.958 ± 0.145 |

The bone density increased after 3 or 6 months treatment for treatment group, but it is of no significant difference (P>0.05). There is no improvement in control group. Also there is no significant difference between the two groups.

2. The results of bone density of collum femoris pre- and after-treatment are shown in table 5:

TABLE 5

Bone density of collum femoris before- and after- treatment in two Groups ($\overline{X} \pm s$, g/cm$^2$)

| Group | Before-treatment | after- 3 months treatment | after- 6 months treatment |
|---|---|---|---|
| Treatment group | 0.736 ± 0.079 | 0.750 ± 0.079** | 0.828 ± 0.124** |
| Control group | 0.748 ± 0.095 | 0.744 ± 0.100 | 0.744 ± 0.093 |

Compared with before-treatment, *P < 0.05, **P < 0.01

There is significant increase in bone density of collum femoris compared between after- and before-treatment within treatment group (P<0.05, P<0.01). But it is of no significant difference within control group.

3. The results of bone density of trigonal area of femur pre- and after-treatment are shown in table 6:

TABLE 6

Bone density of trigonal area of femur before- and after- treatment in two Groups ($\overline{X} \pm s$, g/cm$^2$)

| Group | Before-treatment | after- 3 months treatment | After- 6 months treatment |
|---|---|---|---|
| Treatment group | 0.585 ± 0.104 | 0.600 ± 0.100* | 0.661 ± 0.159**# |
| Control group | 0.582 ± 0.125 | 0.591 ± 0.124 | 0.581 ± 0.134 |

Compared with before-treatment, *P < 0.05, **P < 0.01; compared between control group, #P < 0.05

There is significant increase in bone density of trigonal area of femur compared between after- and before-treatment within treatment group (P<0.05, P<0.01). The bone density of trigonal area of femur increased after 3 months of treatment with no significant difference (P>0.05). And also there is difference between treatment and control groups after 6 months treatment (P<0.05).

4. The results of bone density of trochanteric of femur pre- and after-treatment are shown in table 7:

TABLE 7

Bone density of trochanteric of femur pre- and after- treatment in two Groups ($\overline{X} \pm s$, g/cm$^2$)

| Group | Before-treatment | after- 3 months treatment | after- 6 months treatment |
|---|---|---|---|
| Treatment group | 0.642 ± 0.120 | 0.665 ± 0.125 | 0.752 ± 0.175** |
| Control group | 0.606 ± 0.109 | 0.616 ± 0.099 | 0.616 ± 0.094 |

Compared with before-treatment, P < 0.01; compared between control group, P < 0.01

There is significant difference between before- and after-6-months-treatment in treatment group (P<0.01). And also there is significant difference between treatment and control groups after 6 months treatment (P<0.01).

5. The results of ultrasonic bone density of pre- and after-treatment in two groups are shown in table 8:

TABLE 8 ultrasonic bone density in two groups ($\overline{X} \pm s$, g/cm$^2$)

| Item | Group | n | Before-treatment | after 3 months treatment | after 6 months treatment |
|---|---|---|---|---|---|
| Young adult | Treatment | 16 | −1.875 ± 0.703 | −1.643 ± 0.766** | −1.288 ± 0.857** |
| | Control | 15 | −1.993 ± 0.872 | −1.953 ± 1.181 | −0.593 ± 1.209 |
| Age matched | Treatment | 16 | −1.400 ± 0.700 | −1.200 ± 0.701**# | −0.956 ± 0.682**# |
| | Control | 15 | −1.433 ± 0.788 | −1.386 ± 0.908 | −0.987 ± 1.068 |
| Speed sound | Treatment | 16 | 3769.42 ± 77.61 | 3793.00 ± 81.81**# | 3836.33 ± 99.03**# |
| | control | 15 | 3770.51 ± 89.45 | 3761.77 ± 129.66* | 3804.48 ± 138.89 |

Compared with pretreatment, *P < 0.05, **P < 0.01; compared with control group, #P < 0.05

The difference values between bone density (ultrasonic) of treatment group and those of young adults and age matched increased significantly (P<0.01). And the speed sound increase significantly self-compared within treatment group (P<0.01) and within control group (P<0.05).

Test Example 2

Experimental Study of RDE on Osteoporosis Models in Rats

Observe the effect of RDE in this invention on both Tretinoin-induced and Ovariectomized (OVX) osteoporosis model in rats.

[Material and Methods]
1. Drugs

RDE was produced according to Example 1 (Per gram extract is equivalent to 66.67 g crude drugs). RDE was dissolved in distilled water to a concentration of 0.47 mg/ml before administration. And administration was conducted via gastric tube. Tretinoin is manufactured by *Chongqing Huabang Pharmaceuticals, Ltd.* and was suspended to the concentration of 1.5% with distilled water. Control drug $\alpha$-$D_3$ was manufactured by TEVA PHARMACEUTICALS, Israel, which is solved in distilled water to the concentration of 0.03 μg/ml before using and administrated orally via gastric tube.

2. Animals

Tretinoin-induced osteoporosis rats: sixty female W istar rats, 16-week-old, mean weight 234.85±15.32 g. Ovariectomized rats: sixty female Wistar rats, 12-week-old, mean weight 183.46±12.45 g. All the animals are obtained from the Experimental Animal Center of Chinese Military Medical Academy.

3. Reagents and Instruments

*Bone Biomechanics Rheometer* was manufactured by Stevens Company, Great Britain (model QTS-25). X ray Bone-density-meter was manufactured by Norland Company, USA (model XR-26). The others are all obtained from market.

4. Dose Selections and Groups:
(1) Tretinoin-induced group: Sixty rats are randomly allocated to six groups (10 rats per group). Blank group: control animals received PSS/d (physiological saline solution) alone. Model group: Tretinoin is given orally 70 mg/kg/d; $\alpha$-$D_3$ group: both tretinoin and $\alpha$-$D_3$ are given orally 70 mg/kg/d and 0.002 μg/kg/d respectively; RDE low-dose group: both tretinoin and RDE are given orally 70 mg/kg/d and 54 mg/kg/d respectively; RDE medium-dose group: tretinoin 70 mg/kg/d and RDE 108 mg/kg/d; RDE high-dose group: tretinoin 70 mg/kg/d and RDE 216 mg/kg/d.
(2) Ovariectomized (OVX) rats group: Sixty rats are randomly allocated to six groups (10 rats per group). Blank group is the normal rats. All the other groups are removed amphi-ovaries. Model group received PSS only; $\alpha$-$D_3$ group: $\alpha$-$D_3$ is administrated orally 0.002 μg/kg/d; And RDE is administrated orally in the dose of 54, 108, 216 mg/kg/day to OVX rats respectively, corresponding to RDE groups of low-dose, medium-dose and high-dose.
6. Methods:

The dose administered to each animal is calculated from the individual body weight recorded at the end of each week.

Tretinoin-induced osteoporosis groups: Blank group received PSS during the course of experiment. The other groups commenced treatment on the same day, designated study Day 1, and once-daily tretinoin orally given for 14 days, after which they stopped administrating tretinoin. Both blank and model groups are given PSS in Day 15, and $\alpha$-$D_3$ group is given $\alpha$-$D_3$, RDE groups are given the corresponding dose of RDE orally for 14 days. The final dose is given in the Day 28 before sacrificed. Investigation of Bone Density and Bone-biomechanics are performed in the Day 29.

OVX rats groups: Both blank and model groups are given the same volume of distilled water orally, All the other groups commenced treatment according to the way mentioned above for 12 weeks after which animals are sacrificed and investigation of Bone Density and Bone-biomechanics are performed.

7. Measurements
7.1. Bone density measurements are performed on No.2–4 lumbar spines and right thighbone of each animal.
7.2. Bone biomechanics measurements: three point bending tests of left thighbone of each animal are performed; load-deformation curve is recorded to measure the biomechanics index. Experimental parameters: span 20 mm, loading velocity 10 mm/min. Bone structural mechanics parameters: breaking load, elastic load, maximum radius, elastic radius, maximum energy absorption; bone material mechanics parameters: firstly calculated the Femoral Section Inertial Moment, then computed the maximum strain, elastic strain, maximum stress, elastic stress and elastic modulus according to the formulae.

[Results]
1. Bone Density of Rats in Each Group (Table 9 and 10)

TABLE 9

Bone density of Tretinoin-induced osteoporosis in rats

| | | Bone density (g/cm$^2$) | |
|---|---|---|---|
| Group | n | thighbone | Lumber spine |
| Blank | 10 | 0.146 ± 0.008 | 0.147 ± 0.005 |
| Model | 10 | 0.124 ± 0.006 | 0.129 ± 0.00 |
| $\alpha$-$D_3$ | 10 | 0.137 ± 0.004 | 0.135 ± 0.005 |
| RDE low-dose | 10 | 0.140 ± 0.005 | 0.135 ± 0.005 |
| RDE medium-dose | 10 | 0.140 ± 0.007 | 0.149 ± 0.007 |
| RDE large-dose | 10 | 0.152 ± 0.006 | 0.149 ± 0.011 |

TABLE 10

Bone density of Ovariectomized (OVX) rats group

| | | Bone density (g/cm$^2$) | |
|---|---|---|---|
| Group | n | thighbone | Lumber spine |
| Blank | 10 | 0.14 ± 0.008 | 0.13 ± 0.009 |
| Model | 10 | 0.11 ± 0.007 | 0.11 ± 0.035 |
| $\alpha$-$D_3$ | 10 | 0.13 ± 0.009 | 0.13 ± 0.009 |
| RDE low-dose | 10 | 0.12 ± 0.005 | 0.12 ± 0.005 |
| RDE medium-dose | 10 | 0.12 ± 0.005 | 0.12 ± 0.010 |
| RDE large-dose | 10 | 0.13 ± 0.007 | 0.13 ± 0.004 |

From Table 9 and 10 it is concluded that femoral bone density of RDE groups and $\alpha$-$D_3$ group increased obviously compared with model group. And there is significant differences in elevated degree of femoral bone density compared between RDE groups and $\alpha$-$D_3$ group.

2. Bone Biomechanics Measurements of Rats in Each Group
2.1 The influence on bone structural mechanics indicators, see table 11 and Table 12.

TABLE 11

Bone structural mechanics indicators of Retinoic acid-induced osteoporosis in rats

| Group | n | Maximum load (N) | Maximum strain (mm) | Maximum energy observation (N-mm) | Elastic load (N) | Elastic strain (mm) |
|---|---|---|---|---|---|---|
| Blank | 10 | 146.60 ± 30.80 | 1.54 ± 0.36 | 787.95 ± 130.57 | 159.10 ± 88.80 | 1.65 ± 0.20 |
| Model | 10 | 66.10 ± 11.00 | 0.64 ± 0.10 | 405.88 ± 160.06 | 53.60 ± 19.80 | 0.44 ± 0.18 |
| α-$D_3$ | 10 | 103.20 ± 3.40 | 0.98 ± 0.14 | 635.73 ± 114.46 | 100.40 ± 7.00 | 1.01 ± 0.14 |
| RDE low-dose | 10 | 123.60 ± 6.09 | 1.04 ± 0.13 | 564.38 ± 138.89 | 105.70 ± 4.30 | 1.06 ± 0.09 |
| RDE medium-dose | 10 | 135.30 ± 12.00 | 1.33 ± 0.22 | 655.13 ± 131.46 | 110.00 ± 12.60 | 1.56 ± 0.19 |
| RDE large-dose | 10 | 145.80 ± 11.00 | 1.65 ± 0.25 | 769.62 ± 128.43 | 120.40 ± 8.70 | 1.75 ± 0.16 |

TABLE 12

Bone structural mechanics indicators of Ovariectomized (OVX) rats

| Group | N | Maximum load (N) | Maximum strain (mm) | Elastic load (N) | Elastic strain (N) | Maximum energy observation (N-$mm^2$) |
|---|---|---|---|---|---|---|
| Blank | 10 | 118.3 ± 12.40 | 1.11 ± 0.05 | 96.2 ± 6.00 | 0.93 ± 0.05 | 575.09 ± 138.50 |
| Model | 10 | 76.8 ± 25.00 | 0.68 ± 0.01 | 62.5 ± 2.50 | 0.48 ± 0.07 | 425.25 ± 86.10 |
| α-$D_3$ | 10 | 102.1 ± 2.90 | 0.96 ± 0.10 | 88.6 ± 12.7 | 0.84 ± 0.06 | 520.48 ± 108.44 |
| RDE low-dose | 10 | 97.0 ± 6.50 | 0.71 ± 0.10 | 72.1 ± 7.80 | 0.67 ± 0.09 | 498.55 ± 162.80 |
| RDE medium-dose | 10 | 110.4 ± 10.20 | 0.92 ± 0.06 | 91.6 ± 6.70 | 0.85 ± 0.06 | 543.65 ± 100.78 |
| RDE large-dose | 10 | 134.3 ± 9.50 | 1.10 ± 0.11 | 99.4 ± 4.60 | 0.93 ± 0.05 | 532.37 ± 110.83 |

From above table 11 and 12, the results showed that all the bone structural mechanics indicators in RDE groups and α-$D_3$ group increased significantly compared with model group. Also there is significant differences in the elevated degree of all the bone structural mechanics indicators compared between RDE groups and α-$D_3$ group. And we can see some dose-effect relationship in RDE groups.

2.2 The effect on bone material mechanics indicators, see table 13 and 14.

From table 13 and 14, the results showed that RDE elevated the bone maximum stress, elastic stress, maximum strain, elastic strain and rigidity factor of osteoporosis model rats. And there is significant difference in those indicators compared between RDE group and α-$D_3$ group.

From the results mentioned above, we can see that RDE elevate the bone density, enhance bearing capacity and anti-impact capacity to improve the bone structural mechan-

TABLE 13

Bone material mechanics indicators of Tretinoin-induced osteoporosis in rats

| Group | n | Maximum stress (N/$mm^2$) | Elastic stress (N/$mm^2$) | Maximum strain | Elastic strain | Rigidity coefficient (N/$mm^2$) |
|---|---|---|---|---|---|---|
| Blank | 10 | 309.3 ± 102.8 | 233.2 ± 48.5 | 0.04 ± 0.009 | 0.04 ± 0.013 | 41301 ± 1359 |
| Model | 10 | 122.24 ± 54.8 | 70.9 ± 20.5 | 0.02 ± 0.004 | 0.01 ± 0.004 | 14436 ± 2648 |
| α-$D_3$ | 10 | 167.2 ± 44.5 | 177.6 ± 51.3 | 0.03 ± 0.009 | 0.03 ± 0.01 | 30561 ± 9194 |
| RDE low-dose | 10 | 101.8 ± 3.1 | 79.9 ± 21.1 | 0.04 ± 0.004 | 0.02 ± 0.005 | 14958 ± 2347 |
| RDE medium-dose | 10 | 236.1 ± 59.2 | 217.5 ± 79.2 | 0.03 ± 0.004 | 0.03 ± 0.011 | 24919 ± 2616 |
| RDE large-dose | 10 | 307.9 ± 7.9 | 333.9 ± 27.1 | 0.04 ± 0.001 | 0.04 ± 0.007 | 36893 ± 3704 |

TABLE 14

Bone material mechanics indicators of Ovariectomized (OVX) rats

| Group | N | Maximum stress (N/$mm^2$) | Elastic stress (N/$mm^2$) | Rigidity coefficient | Maximum strain | Elastic strain | Elastic mould | Area of bone cortes |
|---|---|---|---|---|---|---|---|---|
| Blank | 10 | 254.2 ± 32.50 | 197.5 ± 22.40 | 44383 ± 3022 | 0.04 ± 0.003 | 0.04 ± 0.003 | 9516 ± 267 | 6.23 ± 0.52 |
| Model | 10 | 123.4 ± 43.50 | 99.7 ± 8.60 | 34620 ± 11208 | 0.03 ± 0.002 | 0.01 ± 0.002 | 4742 ± 748 | 3.53 ± 0.56 |
| α-$D_3$ | 10 | 221.5 ± 46.50 | 147.2 ± 11.00 | 27508 ± 8073 | 0.03 ± 0.006 | 0.03 ± 0.010 | 7992 ± 1132 | 4.13 ± 0.99 |
| RDE low-dose | 10 | 138.3 ± 41.80 | 151.1 ± 12.50 | 33114 ± 4718 | 0.04 ± 0.004 | 0.03 ± 0.006 | 7233 ± 872 | 4.02 ± 0.07 |
| RDE medium-dose | 10 | 140.0 ± 40.60 | 137.7 ± 10.50 | 32729 ± 3307 | 0.05 ± 0.002 | 0.04 ± 0.002 | 7546 ± 613 | 4.68 ± 0.44 |
| RDE large-dose | 10 | 249.9 ± 18.70 | 208.7 ± 17.80 | 44019 ± 1999 | 0.05 ± 0.003 | 0.04 ± 0.0.04 | 8768 ± 543 | 6.15 ± 0.37 | ics properties, and also has activity to improve geometric configuration and inner material properties.

INDUSTRIAL PRACTICABILITY

RDE in the present invention has the activity to elevate the bone density of osteoporosis patient, to suppress the bone absorption distinctly, and of anti bone-loss. Thereafter the object of treating osteoporosis can be achieved.

What is claimed is:

1. An extract from *Rhizoma Drynariae*, obtained by pulverizing the *Rhizoma*, agitating and extracting the pulverized *Rhizoma* in a mixture of water and alcohol, the temperature of which is below 100° C., wherein the alcohol in the mixture is between 20% and 90% of the water and alcohol mixture by volume, wherein the content of total flavonoids, based on the weight of the extract, is 30 percent or more, and the content of naringin thereof, based on the weight of total flavonoids, is 30 percent or more, and less than 100 percent.

2. The extract according to claim 1, wherein the content of total flavonoids is 50 percent or more.

3. The extract according to claim 2, wherein the content of naringin is 90 percent or less.

4. A pharmaceutical composition comprises the extract of claim 1.

5. The composition according to claim 4, which is used for the treatment of Osteoporosis.

6. A preparation process for a *Rhizoma Drynariae* extract wherein the content of total flavonoids, based on the weight of the extract, is 30 percent or more, and the content of naringin thereof, based on the weight of total flavonoids, is 30 percent or more, and less than 100 percent, the process comprising the steps of:
   1) Extraction of *Rhizoma Drynariae* with water, or a mixture of water and alcohol wherein the alcohol in the mixture is between 20% and 90% of the water and alcohol mixture by volume;
   2) adsorption of the extractant with resin; and
   3) elution of the resin which has absorbed the extractant with water, alcohol or a mixture thereof.

7. The preparation process according to claim 6, wherein the extraction is conducted with water.

8. The preparation process according to claim 6, wherein the extraction is conducted with alcohol/water mixture.

9. The preparation process according to claim 8, wherein the content of alcohol in the alcohol/water mixture is 40–90% (wt %).

10. The preparation process according to claim 9, wherein the alcohol is selected from methanol and ethanol.

11. The preparation process according to claim 10, wherein the alcohol is ethanol.

12. The preparation process according to claim 6, wherein the resin is macropore adsorption resin.

13. The preparation process according to claim 6, wherein said resin is washed by water after adsorption of the extractant, before the elution with alcohol or alcohol/water mixture.

14. The preparation process according to claim 13, wherein the elution is conducted with alcohol/water mixture.

15. The preparation process according to claim 14, wherein the content of alcohol is 40–90% (wt %) of the alcohol/water mixture.

16. The preparation process according to claim 14, wherein the alcohol is selected from methanol and ethanol.

17. The preparation process according to claim 16, wherein the alcohol is ethanol.

18. An extract of *Rhizoma Drynariae*, prepared by the process of:
   1) extracting *Rhizoma Drynariae* using a mixture of water and alcohol, the alcohol concentration being between 20 and 90% by volume;
   2) adsorbing the extract with a resin; and
   3) after the extract has been adsorbed by said resin, eluting the resin with a mixture of water and alcohol.

19. A method of extracting *Rhizoma Drynariae*, comprising the steps of:
   1) extracting *Rhizoma Drynariae* using a mixture of water and alcohol, the alcohol concentration being between 20 and 90% by volume;
   2) adsorbing the extract with a resin; and
   3) after the extract has been adsorbed by said resin, eluting the resin with a mixture of water and alcohol.

20. The method of claim 19 wherein the resin is eluted using a mixture of water and alcohol, said alcohol being less than 50% of the mixture by volume.

21. An extract from *Rhizoma Drynariae*, obtained by pulverizing the *Rhizoma*, agitating and extracting the pulverized *Rhizoma* in water, the temperature of which is under 100° C., wherein the alcohoi in the mixture is between 20% and 90% of the water and alcohol mixture by volume, wherein the content of total flavonoids, based on the weight of the extract, is 30 percent or more, and the content of naringin thereof, based on the weight of total flavonoids, is 30 percent or more, and less than 100 percent.

* * * * *